United States Patent
Lee et al.

(10) Patent No.: US 9,414,809 B2
(45) Date of Patent: Aug. 16, 2016

(54) PROBE FOR ULTRASONIC DIAGNOSTIC APPARATUS AND METHOD OF MANUFACTURING THE SAME

(75) Inventors: Sung Jae Lee, Seoul (KR); Jung Lim Park, Seoul (KR); Jae Yk Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 706 days.

(21) Appl. No.: 12/912,656

(22) Filed: Oct. 26, 2010

(65) Prior Publication Data
US 2011/0105906 A1    May 5, 2011

(30) Foreign Application Priority Data

Oct. 29, 2009  (KR) .................. 10-2009-0103771

(51) Int. Cl.
*A61B 8/00*  (2006.01)
*B06B 1/06*  (2006.01)
*G10K 11/00*  (2006.01)

(52) U.S. Cl.
CPC .............. *A61B 8/4281* (2013.01); *B06B 1/0622* (2013.01); *G10K 11/004* (2013.01); *Y10T 29/49005* (2015.01)

(58) Field of Classification Search
CPC .. A61B 8/4281; B06B 1/0622; G10K 11/004; Y10T 29/49005
USPC ............................................ 600/459; 29/594
See application file for complete search history.

(56) References Cited

U.S. PATENT DOCUMENTS

| | | | |
|---|---|---|---|
| 5,329,682 A | 7/1994 | Thurn et al. | |
| 2003/0138121 A1* | 7/2003 | Reck et al. ............. | 381/190 |
| 2005/0236930 A1 | 10/2005 | Hasegawa et al. | |
| 2007/0145860 A1 | 6/2007 | Aoki et al. | |
| 2008/0312537 A1* | 12/2008 | Hyuga .......... | B06B 1/0622 |
| | | | 600/459 |
| 2010/0317972 A1* | 12/2010 | Baumgartner et al. ....... | 600/459 |

FOREIGN PATENT DOCUMENTS

| | | |
|---|---|---|
| DE | 3401979 A1 | 7/1985 |
| EP | 2 206 466 A1 | 7/2010 |
| JP | 4-336799 B2 | 11/1992 |
| JP | 4-347146 B2 | 12/1992 |
| JP | 2001-276060 A | 10/2001 |

(Continued)

OTHER PUBLICATIONS

European Search Report issued in European Patent Application No. 10187084.8-2319, mailed Feb. 17, 2011.
Korean Office Action issued in Korean Patent Application No. KR 10-2009-0103771 dated Jul. 3, 0211.

(Continued)

*Primary Examiner* — Jonathan Cwern
(74) *Attorney, Agent, or Firm* — McDermott Will & Emery LLP

(57) ABSTRACT

A probe for an ultrasonic diagnostic apparatus and a method of manufacturing the same are disclosed. The probe includes a sound matching layer having a mounting groove, a piezoelectric member mounted on the mounting groove, a first connector interconnected to the sound matching layer, and a second connector interconnected to the piezoelectric member. The probe permits interconnection of the piezoelectric member to the first and second connectors to be performed rapidly and easily through a single bonding operation, thereby reducing manufacturing time while facilitating the manufacture of the probe.

7 Claims, 4 Drawing Sheets

(56) References Cited

FOREIGN PATENT DOCUMENTS

| | | |
|---|---|---|
| JP | 2002-247696 A | 8/2002 |
| JP | 2003-244793 A | 8/2003 |
| JP | 2009-177342 A | 8/2009 |

OTHER PUBLICATIONS

Japanese Office Action issued in Japanese Application No. 2010-229963 dated Jun. 24, 2014.
Japanese Office action issued in Japanese Application No. 2010-229963 dated Jan. 13, 2015, w/English translation.

\* cited by examiner

PROBE FOR ULTRASONIC DIAGNOSTIC APPARATUS AND METHOD OF MANUFACTURING THE SAME

CROSS REFERENCE TO RELATED APPLICATIONS

This application claims the benefit of Korean Patent Application No. 10-2009-0103771, filed on Oct. 29, 2009, the entire contents of which are incorporated herein by reference.

BACKGROUND OF THE INVENTION

1. Field of the Invention

The present invention relates to probes and, more particularly, to a probe for an ultrasonic diagnostic apparatus that generates internal images of a patient body using ultrasound waves, and a method of manufacturing the same.

2. Description of the Related Art

Generally, an ultrasonic diagnostic apparatus refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasonic diagnostic apparatus has been widely used for diagnosis of the heart, the abdomen, the urinary organs, and in obstetrics and gynecology due to various merits such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

The ultrasonic diagnostic apparatus includes a probe which transmits an ultrasound signal to a patient body and receives the ultrasound echo-signal reflected therefrom to obtain the ultrasound image of the patient body.

The probe includes a transducer, a case with an open upper end, a cover coupled to the open upper end of the case to directly contact the body surface of the patient, and the like.

The transducer includes a piezoelectric layer in which a piezoelectric material converts electrical signals into sound signals or vice versa while vibrating, a sound matching layer reducing a difference in sound impedance between the piezoelectric layer and a patient body to allow as much of the ultrasound waves generated from the piezoelectric layer as possible to be transferred to the patient body, a lens layer focusing the ultrasound waves, which travel in front of the piezoelectric layer, onto a predetermined point, and a backing layer blocking the ultrasound waves from traveling in a rearward direction of the piezoelectric layer to prevent image distortion.

The piezoelectric layer includes a piezoelectric member and electrodes provided to upper and lower ends of the piezoelectric member, respectively. Further, a printed circuit board (PCB) is bonded to the piezoelectric layer. The PCB is provided with wiring electrodes that are connected to the electrodes of the piezoelectric layer to transfer signals from the piezoelectric member. The PCB is connected to the piezoelectric layer by connecting the wiring electrodes of the PCB to the electrodes of the piezoelectric layer.

In fabrication of the probe as above, connection between the wiring electrodes of the PCB and the electrodes of the piezoelectric layer is a laborious operation, which requires significant fabrication time and causes deterioration in performance of the probe due to low durability and non-uniformity on the connection therebetween. Therefore, there is a need to solve such problems.

SUMMARY OF THE INVENTION

The present invention is conceived to solve the problems of the related art as described above, and an aspect of the present invention is to provide an improved probe for an ultrasonic diagnostic apparatus configured to allow easy manufacture of the probe while preventing deterioration in performance caused by defective connection between a piezoelectric layer and a PCB, and a method of manufacturing the same.

In accordance with one aspect of the invention, a probe for an ultrasonic diagnostic apparatus includes a sound matching layer having a mounting groove; a piezoelectric member having an upper face and a lower face, the piezoelectric member mounted within the mounting groove such that the upper face is coupled to the sound matching layer; a first connector coupled to the sound matching layer; and a second connector coupled to the first connector and to the lower face of the piezoelectric member.

The mounting groove may include a contact part formed parallel to the piezoelectric member and coupled to the upper face of the piezoelectric member; and an extension part extending from the contact part towards the first connector.

The first connector may be coupled to the extension part. The first connector may include a right first connector and a left first connector. The right first connector may be coupled to the extension part and the second connector. The left first connector may be coupled to the extension part and the second connector.

The mounting groove may have a bracket ("ㄷ") shape.

The first connector and the second connector may include a flexible printed circuit board (FPCB).

In accordance with another aspect of the invention, a method of manufacturing a probe for an ultrasonic diagnostic apparatus may include stacking a first connector on a second connector; stacking a piezoelectric member on the second connector between the first connector; stacking a sound matching layer having a mounting groove on the piezoelectric member and the first connector so that the piezoelectric member is disposed within the mounting groove; and coupling a lower face of the piezoelectric member and the second connector, an upper face of the piezoelectric member and the sound matching layer, and the sound matching layer and the first connector through a single bonding operation.

In the coupling through a single bonding operation, the first connector may be coupled only to the sound matching layer.

As such, the probe for an ultrasonic diagnostic apparatus and the method of manufacturing the same according to one embodiment can eliminate laborious operation such as soldering or welding, and permit interconnection of a piezoelectric member to first and second connectors to be performed rapidly and easily through a single bonding operation, thereby reducing manufacturing time while facilitating the manufacture of the probe.

Further, according to the embodiment, the interconnection of the piezoelectric member to the first and second connectors may be performed with the first and second connectors stably positioned, so that durability and uniformity of connected portions are enhanced, thereby preventing deterioration in performance of the probe due to failure of the connection between the piezoelectric member and the first and second connectors.

Further, according to the embodiment, since the first connector is connected to the piezoelectric member via the sound matching layer instead of being directly connected thereto, the first connector is not disposed between the backing layer and the piezoelectric layer, so that performance of the piezoelectric member can be enhanced and the length of the first connector is decreased while reducing influence of impedance, thereby reducing manufacturing costs.

BRIEF DESCRIPTION OF THE DRAWINGS

The above and other aspects, features and advantages of the invention will become apparent from the following description of embodiments given in conjunction with the accompanying drawings, in which.

DETAILED DESCRIPTION OF THE EMBODIMENT

Exemplary embodiments of the invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the invention into account and can be changed according to the custom or intention of users or operators. Therefore, definition of the terms should be made according to overall disclosures set forth herein.

Figure 1:
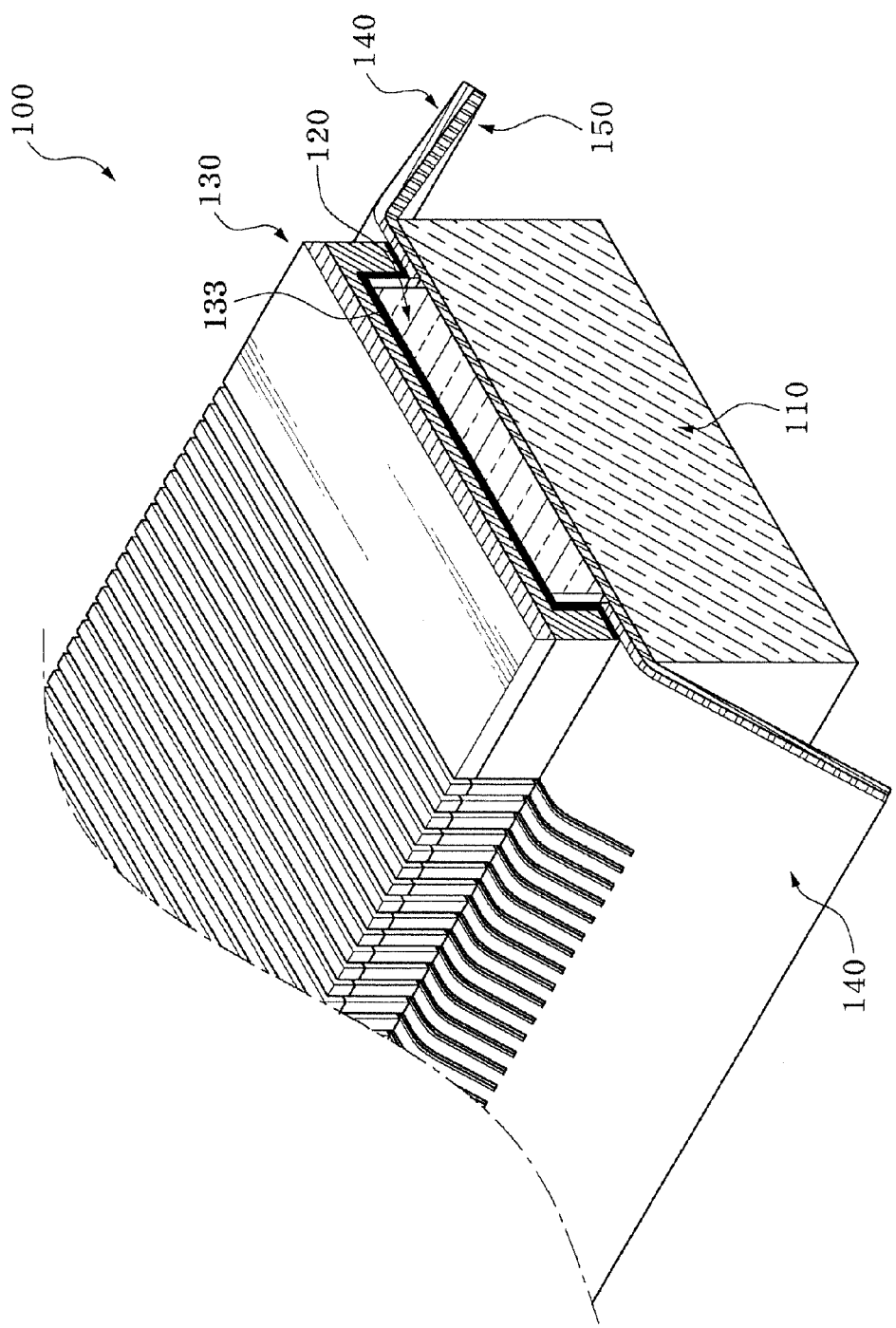
FIG. 1 is a perspective view of a probe for an ultrasonic diagnostic apparatus according to one embodiment of the present invention.
Figure 2:
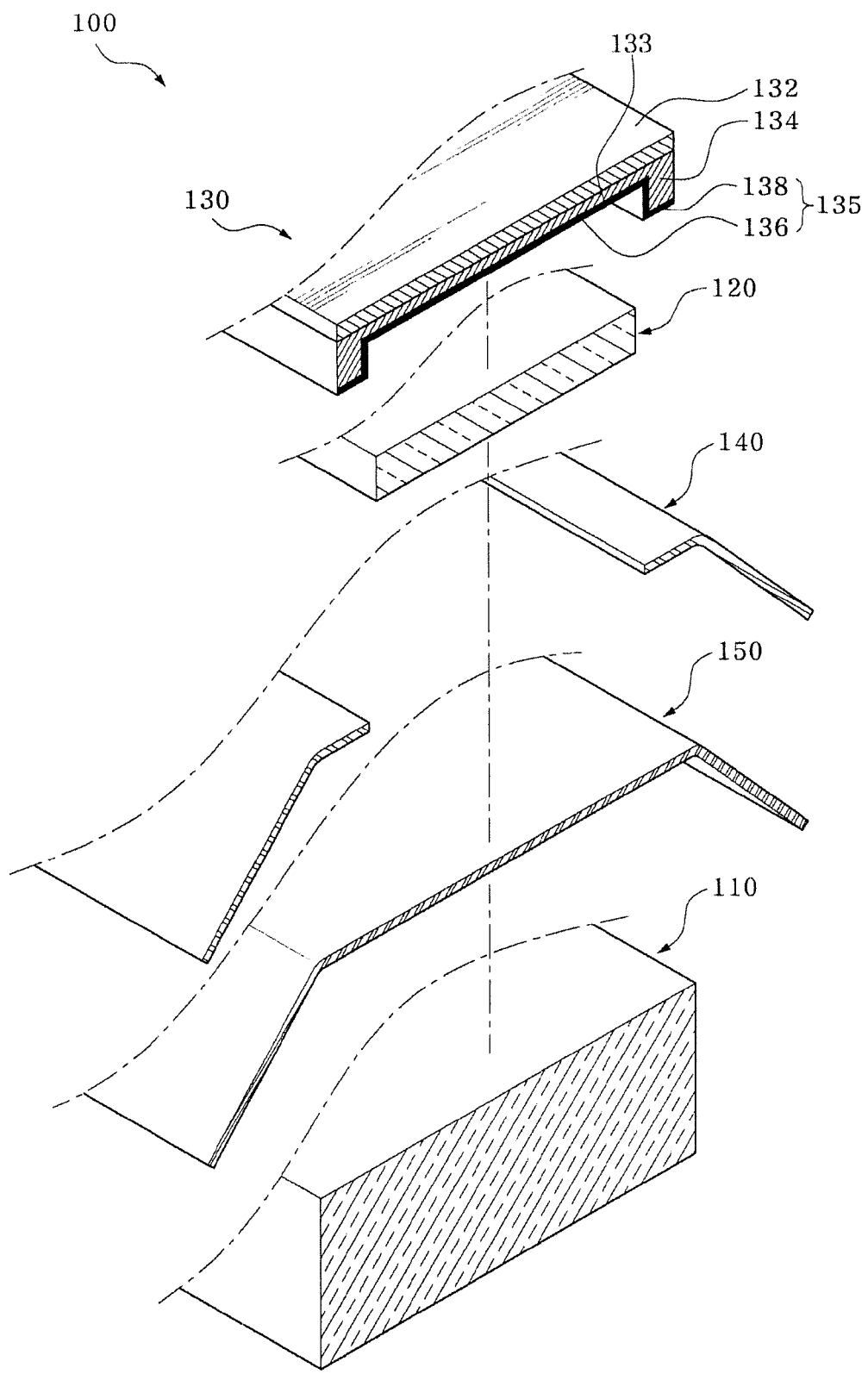
FIG. 2 is an exploded perspective view of the probe shown in FIG. 1.
Figure 3:
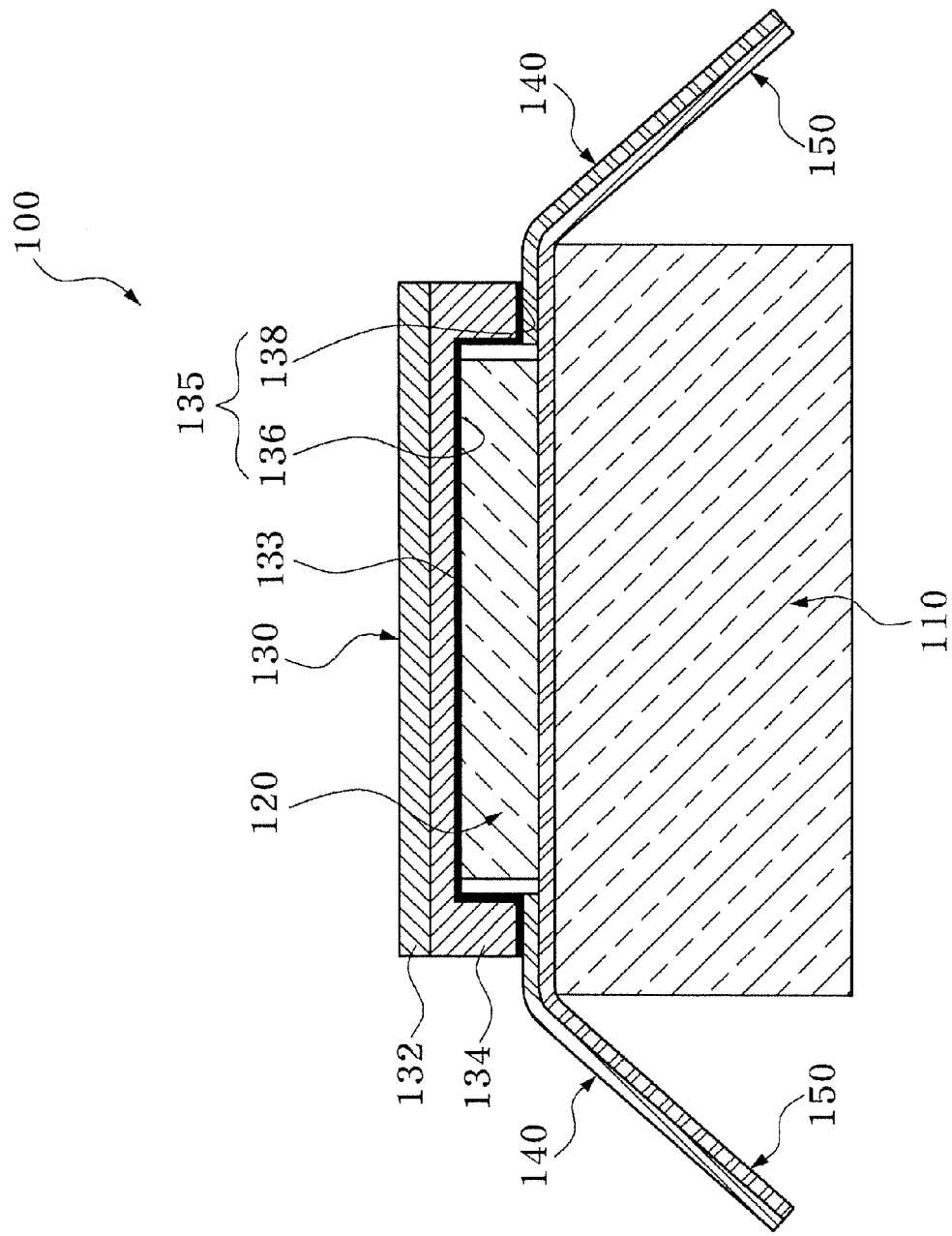
FIG. 3 is a cross-sectional view of the probe shown in FIG. 1.

FIG. 1 is a perspective view of a probe for an ultrasonic diagnostic apparatus according to one embodiment of the invention, FIG. 2 is an exploded perspective view of the probe shown in FIG. 1, and FIG. 3 is a cross-sectional view of the probe shown in FIG. 1.

Referring to FIGS. 1 to 3, a probe 100 for an ultrasonic diagnostic apparatus according to this embodiment includes a backing layer 110, a piezoelectric member 120, a sound matching layer 130, a first connector 140, and a second connector 150.

The backing layer 110 is disposed behind the piezoelectric member 120. The backing layer 110 reduces a pulse width of an ultrasound wave by suppressing free vibration of the piezoelectric member 120 and prevents image distortion by blocking unnecessary propagation of the ultrasound wave in the rearward direction of the piezoelectric member 120. The backing layer 110 may be formed of a material containing a rubber to which epoxy, tungsten powder, and the like are added.

The piezoelectric member 120 is disposed in front of the backing layer 110. The piezoelectric member 120 generates ultrasound waves using a resonance phenomenon and may be formed of a ceramic of lead zirconate titanate (PZT), a PZNT single crystal made of a solid solution of lead zinc niobate and lead titanate, a PZMT single crystal made of a solid solution of lead magnesium niobate and lead titanate, or the like.

The piezoelectric member 120 is formed with electrodes (not shown). According to this embodiment, the electrodes are formed on opposite sides of the piezoelectric member 120, that is, on a front side and a rear side of the piezoelectric member 120, respectively. The electrodes may be formed of a highly conductive metal such as gold, silver, or copper.

One of the electrodes formed on the opposite sides of the piezoelectric member 120 corresponds to a positive electrode (signal electrode) of the piezoelectric member 120 and the other corresponds to a negative electrode (ground electrode) of the piezoelectric member 120. The electrodes are formed such that the positive electrode is separated from the negative electrode. In this embodiment, the electrode formed on one side of the piezoelectric member 120 is illustrated as the negative electrode, and the electrode formed on the other side of the piezoelectric member 120 is illustrated as the positive electrode.

The sound matching layer 130 is disposed in front of the backing layer 110. The sound matching layer 130 allows ultrasound signals generated from the piezoelectric member 120 to be efficiently transferred to a target by matching sound impedances of the piezoelectric member 120 and the target. The sound matching layer 130 is configured to have an intermediate value between the sound impedance of the piezoelectric member 120 and the sound impedance of the target. The sound matching layer 130 may be formed of a glass or resin material.

In this embodiment, the sound matching layer 130 is illustrated as including a first sound matching layer 132 and a second sound matching layer 134, which are formed of different materials to allow the sound impedance to be changed stepwise from the piezoelectric member 120 to the target.

The sound matching layer 130 is provided with a mounting groove 135. In this embodiment, the mounting groove 135 is illustrated as being formed on the second sound matching layer 134. The mounting groove 135 is formed to have a bracket ("⊏") shape open towards the backing layer 110. According to this embodiment, the piezoelectric member 120 is mounted on the mounting groove 135. The mounting groove 135 includes a contact part 136 and an extension part 138.

The contact part 136 is formed parallel to the piezoelectric member 120 and contacts the piezoelectric member 120. The contact part 136 is disposed in front of the piezoelectric member 120 to contact one side of the piezoelectric member 120.

The extension part 138 extends from the contact part 136 to the first connector 140. In this embodiment, the extension part 138 extends from opposite ends of the contact part 136 to the first connector 140. The extension part 138 is disposed at lateral sides of the piezoelectric member 120 to be separated therefrom.

The mounting groove 135 including the contact part 136 and the extension part 138 has the bracket ("⊏") shape open towards the backing layer 110. With this configuration, the piezoelectric member 120 mounted on the mounting groove 135 has upper and opposite lateral sides, that is, three sides thereof, surrounded by the contact part 136 and the extension part 138.

The sound matching layer 130 is interconnected to the piezoelectric member 120, so that electric connection between the sound matching layer 130 and the piezoelectric member 120 can be obtained.

In one example, the sound matching layer 130 is provided with electrodes 133. The electrodes 133 may be provided to the second sound matching layer 134, specifically, to the mounting groove 135 so as to be provided to the entirety of the mounting groove 135 including the contact part 136 and the extension part 138.

The electrodes 133 formed on the sound matching layer 130 are electrically connected to the electrodes formed on one side of the piezoelectric member 120, so that the sound matching layer 130 is interconnected to the piezoelectric member 120 via the electrodes electrically connected to one another. The electrodes may be formed of a 20 highly electrically conductive material, such as gold, silver or copper, by deposition, sputtering, plating, spraying or the like.

In another example, the sound matching layer 130 is directly connected to the piezoelectric member 120. That is, the sound matching layer 130 is formed of the conductive material, such as gold, silver or copper, and directly electrically connected to the piezoelectric member 120.

The sound matching layer 130 is electrically connected to the electrodes formed on the one side of the piezoelectric member 120, so that interconnection between the sound matching layer 130 and the piezoelectric member 120 is obtained.

In the sound matching layer 130 formed of the electrically conductive material, the entirety of the sound matching layer 130 including the first and second sound matching layers 132, 134 may be formed of the electrically conductive material, or only the second sound matching layer 134 connected to the piezoelectric member 120 may be formed of the electrically conductive material. Since the sound matching layer 130 is electrically connected to the electrodes formed on the one side of the piezoelectric member 120 without a separate electrode, interconnection between the sound matching layer 130 and the piezoelectric member 120 can be obtained.

The first connector 140 is interconnected to the sound matching layer 130. In this embodiment, the first connector 140 includes, but is not limited to, a flexible printed circuit board (FPCB). The first connector 140 may include a printed circuit board or any configuration capable of supplying signals or electricity as well as the printed circuit board (PCB).

The first connector 140 is formed with wiring electrodes (not shown). The wiring electrodes are formed on surfaces of the first connector 140 contacting the sound matching layer 130 and are electrically connected to the sound matching layer 130.

The first connector 140 is respectively disposed on the opposite lateral sides of the sound matching layer 130 on which the extension part 138 is located. Each of the first connector 140 contacts the extension part 138 in a state of being inserted into a space between the extension part 138 and the backing layer 110.

Each of the first connector 140 contacting the extension part 138 is interconnected to the extension part 138 via the wiring electrodes electrically connected to the extension part 138.

In this embodiment, the first connector 140 is disposed so as not to overlap the piezoelectric member 120 and is interconnected only to the extension part 138. Herein, the interconnection of the first connector 140 only to the extension part 138 means that the first connector 140 is interconnected only to the sound matching layer 130 through interconnection between the first connector 140 and the extension part 138, and does not mean that the first connector 140 is not interconnected to other parts of the sound matching layer 130, for example, the contact part 136 of the sound matching layer 130.

The first connector 140 is interconnected to the sound matching layer 130 through the extension part 138, and are interconnected only to one side of the piezoelectric member 120 through the contact part 136 of the sound matching layer 130 without interconnection to the other side of the piezoelectric member 120.

The second connector 150 is interconnected to the piezoelectric member 120. In this embodiment, the second connector 150 includes, but is not limited to, a flexible printed circuit board (FPCB). The second connector 150 may include a printed circuit board or any configuration capable of supplying signals or electricity as well as the printed circuit board (PCB).

The second connector 150 is formed with wiring electrodes (not shown). The wiring electrodes are formed on a surface of the second connector 150 contacting the other side of the piezoelectric member 120 and are electrically connected to the other side of the piezoelectric member 120.

According to this embodiment, the second connector 150 is disposed in front of the backing layer 110 to contact the other side of the piezoelectric member 120. The second connector 150 is interconnected to the other side of the piezoelectric member 120 via electrical connection between the wiring electrodes and the electrodes formed on the other side of the piezoelectric member 120.

On the other hand, although not shown in the drawings, the probe for an ultrasonic diagnostic apparatus according to this embodiment may further include a lens layer (not shown) disposed in front of the sound matching layer 130 to focus forwardly traveling ultrasound waves on a predetermined point.

Figure 4:
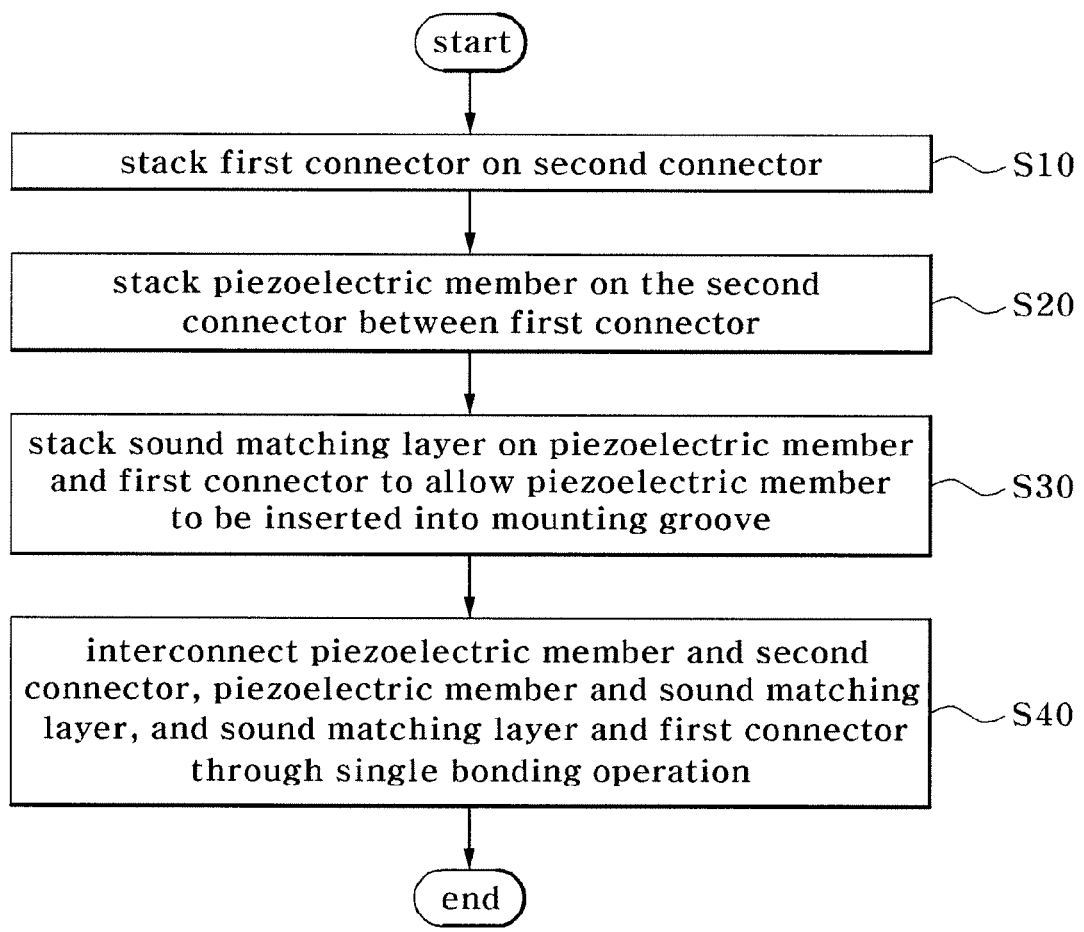
FIG. 4 is a flowchart of a method of manufacturing a probe for an ultrasonic diagnostic apparatus according to one embodiment of the invention.

FIG. 4 is a flowchart of a method of manufacturing a probe for an ultrasonic diagnostic apparatus according to one embodiment of the invention.

Next, referring to FIGS. 1 to 4, a method of manufacturing a probe for an ultrasonic diagnostic apparatus according to one embodiment will be described.

To manufacture the probe according to this embodiment, a first connector 140 is stacked on a second connector 150, in S10.

Here, each of the first connector 140 is stacked on a front side of the second connector 150, that is, on a side of the second connector 150 having wiring electrodes of the second connector 150 formed thereon, to be separated from the second connector 150 such that the wiring electrodes of the second connector 150 are exposed between the first connector 140. Preferably, the first connector 140 is separated from each other by a distance corresponding to the distance between an extension part 138 at one side of a mounting groove 135 and an extension part 138 at the other side of the mounting groove 135 provided to a sound matching layer 130.

The first connector 140 and the second connector 150 are stacked on a backing layer 110. Here, the first connector 140 and the second connector 150 may be stacked as a stacked assembly on the backing layer 110 or may be stacked thereon in such a way of stacking the second connector 150 on the backing layer 110, followed by stacking the first connector 140 on the second connector 150.

Then, a piezoelectric member 120 is stacked on the second connector 150 between the first connector 140, in S20. That is, the piezoelectric member 120 is stacked in front of the second connector 150 to be disposed on the portion of the second connector 150 exposed between the first connector 140.

As a result, the second connector 150 is interconnected to the piezoelectric member 120 by electrical connection of the second connector 150 to electrodes formed on one side of the piezoelectric member 120, and the first connector 140 is disposed so as not to overlap the piezoelectric member 120.

Additionally, the sound matching layer 130 is mounted on the piezoelectric member 120 and the first connector 140 such that the piezoelectric member 120 is inserted into the mounting groove 135, in S30.

When the sound matching layer 130 is stacked on the piezoelectric member 120 and the first connector 140, one side of the piezoelectric member 120 contacts a contact part 136 of the mounting groove 135, and the first connector 140 is disposed so as not to overlap the piezoelectric member 120 and contacts the extension part 138 of the mounting groove 135.

As a result, the piezoelectric member 120 is electrically connected to the contact part 136 through the electrodes formed on the one side of the piezoelectric member 120 to interconnect with the sound matching layer 130, and the first connector 140 is electrically connected to the extension part 138 through the wiring electrodes to interconnect with the sound matching layer 130.

The piezoelectric member 120 may be interconnected to the first connector 140 by the interconnections between the piezoelectric member 120 and the sound matching layer 130 and between the first connector 140 and the sound matching layer 130.

Then, the stacked piezoelectric member 120, sound matching layer 130, first connector 140 and second connector 150 are interconnected through a single bonding operation. That is, interconnection between one side of the piezoelectric member 120 and the sound matching layer 130, interconnection between the other side of the piezoelectric member 120 and the second connector 150, interconnection between the sound matching layer 130 and the first connector 140 is obtained through the single bonding operation, in S40. Here, the first connector 140 may be interconnected only to the sound matching layer 130. The bonding operation may be carried out using conductive or non-conductive adhesives.

On the other hand, in this embodiment, the first connector 140 is stacked on the second connector 150, and the piezoelectric member 120 is stacked on the second connector 150, followed by stacking the sound matching layer 130 on the piezoelectric member 120 and the first connector 140. However, it should be noted that the method of manufacturing a probe for an ultrasonic diagnostic apparatus is not limited to the sequence described above, and the processes of the method may be performed in a different sequence or at the same time.

In the method of manufacturing a probe for an ultrasonic diagnostic apparatus, the stacked piezoelectric member 120, sound matching layer 130, first connector 140 and second connector 150 are interconnected through a single bonding operation, instead of complicated and laborious operation of directly connecting the individual wiring electrodes of the first and second connectors 140, 150 to the electrodes of the piezoelectric member 120 with the first and second electrodes 140, 150 not stably positioned, so that the first and second connectors 140, 150 may be interconnected to the piezoelectric member 120.

The probe 100 for an ultrasonic diagnostic apparatus manufactured by the method according to the embodiment permits interconnection of the piezoelectric member 120 to the first and second connectors 140, 150 to be performed rapidly and easily through a single bonding operation, thereby reducing manufacturing time while facilitating the manufacture of the probe.

Further, the probe according to the embodiment allows interconnection of the piezoelectric member 120 to the first and second connectors 140, 150 to be performed, with the first and second connectors 140, 150 stably positioned, so that durability and uniformity of connected portions are enhanced, thereby preventing deterioration in performance of the probe due to failure of the connection between the piezoelectric member 120 and the first and second connectors 140, 150.

Further, according to the embodiment, since the first connector 140 is connected to the piezoelectric member 120 via the sound matching layer 130 instead of being directly connected thereto, the first connector 140 is not disposed between the backing layer 110 and the piezoelectric layer 120, so that performance of the piezoelectric member 120 can be enhanced and the length of the first connector 140 is decreased while reducing influence of impedance, thereby reducing manufacturing costs.

Although some embodiments have been provided to illustrate the invention in conjunction with the drawings, it will be apparent to those skilled in the art that the embodiments are given by way of illustration only, and that various modifications and equivalent embodiments can be made without departing from the spirit and scope of the invention. The scope of the invention should be limited only by the accompanying claims.

What is claimed is:

1. A probe for an ultrasonic diagnostic apparatus, comprising:
   a sound matching layer having a mounting groove, a first electrode formed on the sound matching layer;
   a piezoelectric member having an upper face and a lower face, the piezoelectric member mounted within the mounting groove such that the upper face is coupled to the sound matching layer, a second electrode formed on the piezoelectric member;
   a first connector coupled to the sound matching layer; and
   a second connector coupled to the first connector and to the lower face of the piezoelectric member,
   wherein the mounting groove comprises:
      a contact part formed parallel to the piezoelectric member and coupled to the upper face of the piezoelectric member; and
      an extension part extending from the contact part towards the first connector,
   wherein the first electrode is provided in a shape corresponding to the contact part and the extension part so as to contact the second electrode formed on one side of the piezoelectric member,
   wherein the first electrode is provided to the entirety of the mounting groove including the contact part and the extension part,
   wherein the first connector is coupled to the first electrode provided on the extension part, and
   wherein the first connector is arranged between the extension part and the second connector.

2. The probe according to claim 1, wherein the first connector comprises a right first connector and a left first connector.

3. The probe according to claim 2, wherein the right first connector is coupled to the extension part and the second connector, and the right first connector and the second connector are adjacent one another.

4. The probe according to claim 2, wherein the left first connector is coupled to the extension part and the second connector, and the left first connector and the second connector are adjacent one another.

5. The probe according to claim 1, wherein the first connector comprises a flexible printed circuit board (FPCB).

6. The probe according to claim 1, wherein the second connector comprises a flexible printed circuit board (FPCB).

7. The probe according to claim 1, wherein the first connector is disposed on a portion of the first electrode that does not contact the piezoelectric member.

* * * * *